(12) United States Patent
Childress et al.

(10) Patent No.: US 12,144,904 B2
(45) Date of Patent: Nov. 19, 2024

(54) ELECTROMAGNETIC INTERFERENCE REDUCING SYSTEMS AND METHODS FOR ULTRAVIOLET LAMP ASSEMBLIES

(71) Applicant: THE BOEING COMPANY, Chicago, IL (US)

(72) Inventors: Jamie J. Childress, Mercer Island, WA (US); Jeffrey Scott Bissell, Auburn, WA (US)

(73) Assignee: The Boeing Company, Chicago, IL (US)

( * ) Notice: Subject to any disclaimer, the term of this patent is extended or adjusted under 35 U.S.C. 154(b) by 413 days.

(21) Appl. No.: 17/703,209

(22) Filed: Mar. 24, 2022

(65) Prior Publication Data

US 2022/0362416 A1 Nov. 17, 2022

Related U.S. Application Data

(60) Provisional application No. 63/186,849, filed on May 11, 2021.

(51) Int. Cl.
*A61L 2/10* (2006.01)
*H05K 9/00* (2006.01)

(52) U.S. Cl.
CPC .............. *A61L 2/10* (2013.01); *H05K 9/0058* (2013.01); *A61L 2202/10* (2013.01)

(58) Field of Classification Search
CPC ...... A61L 2/10; A61L 2202/10; H05K 9/0058
See application file for complete search history.

(56) References Cited

U.S. PATENT DOCUMENTS

| | | |
|---|---|---|
| 6,252,180 B1 | 6/2001 | Buskmiller |
| 2003/0013048 A1 | 1/2003 | Gilson |
| 2018/0064833 A1 * | 3/2018 | Childress ............... B64D 11/02 |

OTHER PUBLICATIONS

1 Extended European Search Report for EP 22172669.8-1012, dated Oct. 18, 2022.

* cited by examiner

*Primary Examiner* — Nicole M Ippolito
*Assistant Examiner* — Hanway Chang
(74) *Attorney, Agent, or Firm* — Joseph M. Butscher; The Small Patent Law Group LLC

(57) ABSTRACT

An ultraviolet (UV) light sanitizing system includes an electromagnetic interference (EMI) reducing cover configured to couple to a housing of a UV lamp assembly having a UV light source that is configured to emit UV light through a light outlet of the housing. The EMI reducing cover is further configured to be disposed one or more of within, below, or over the light outlet. The EMI reducing cover includes one or more grids including beams and light openings defined between the beams. The light openings provide open areas through which the UV light emitted from the UV light source passes, and wherein the EMI reducing cover includes at least 90% open space. In at least one embodiment, the beams include at least one surface that is transverse to a direction of the UV light that is to be emitted from the UV light source. In at least one embodiment, wherein the EMI reducing cover includes an interior grid and an exterior grid.

23 Claims, 8 Drawing Sheets

ABSTRACT# ELECTROMAGNETIC INTERFERENCE REDUCING SYSTEMS AND METHODS FOR ULTRAVIOLET LAMP ASSEMBLIES

CROSS-REFERENCE TO RELATED APPLICATIONS

This application relates to and claims priority benefits from U.S. Provisional Patent Application No. 63/186,849, filed May 11, 2021, which is hereby incorporated by reference in its entirety.

FIELD OF THE DISCLOSURE

Embodiments of the present disclosure generally relate to systems and methods for reducing (for example, suppressing) electromagnetic interference (EMI) in relation to ultraviolet (UV) lamp assemblies.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light.

For example, a UV sanitizing system includes a UV lamp assembly having a UV light emitter, such as an excimer bulb. During operation, the excimer bulb generates EMI. In aircraft or other EMI sensitive vehicles, in particular, a Faraday cage can be used to suppress the EMI.

However, a light outlet (such as a window, aperture, or the like) of a UV lamp assembly needs to be as open as possible to allow passage of as much UV light as possible. As can be appreciated, a Faraday cage positioned at the light outlet blocks some of the UV light.

A known EMI reducing cover for a UV lamp assembly typically includes a round wire mesh or flat cut grid. However, in both cases, UV light that impinges on the wire mesh or grid is reflected back toward the UV light source, thereby reducing the amount of UV light that passes out of the UV lamp assembly.

SUMMARY OF THE DISCLOSURE

A need exists for a system and a method for reducing EMI in relation to UV lamp assemblies. Further, a need exists for a system and a method for reducing EMI while also allowing passage of a significant amount of UV light (for example, as much UV light as possible) from a UV lamp assembly.

With those needs in mind, certain embodiments provide an electromagnetic interference (EMI) reducing cover configured to couple to a housing of a UV lamp assembly having a UV light source that is configured to emit UV light through a light outlet of the housing. The EMI reducing cover includes one or more grids comprising a plurality of structural beams that define a plurality of light openings. The plurality of light openings facilitate passage of the UV light emitted from the UV light source. The EMI reducing cover includes at least 90 percent open space relative to the plurality of the plurality of structural beams. In at least one embodiment, the EMI reducing cover is not configured to be directly coupled to the UV light source.

In at least one embodiment, the plurality of structural beams are formed of a reflective material.

In at least one embodiment, a pitch of the EMI reducing cover is 0.3 inches or less, and a thickness of each of the beams is 0.02 inches or less. For example, a pitch of the EMI reducing cover is 0.2935 inches, and a thickness of each of the beam is 0.01 inches.

In at least one embodiment, a ratio of a pitch of the EMI reducing cover to a thickness of each of the beams is at least 15:1. For example, a ratio of a pitch of the EMI reducing cover to a thickness of each of the beams is 29.35:1. As another example, a ration of a pitch of the EMI reducing cover to a thickness of each of the beams is 30:1.

In at least one embodiment, the EMI reducing cover further includes an outer frame. The plurality of structural beams and the plurality of light openings are disposed inboard from the outer frame. The outer frame is configured to be secured to the housing.

In at least one embodiment, the beams include at least one surface that is transverse to a direction of the UV light that is to be emitted from the UV light source. For example, the at least one surface is configured to face the UV light source, and the at least one surface includes a reflective material that facilitates reflecting at least some of the UV light through the one or more light openings. As a further example, the at least one surface includes two surfaces that are transverse to the direction of the UV light that is to be emitted from the UV light source. As an example, the plurality of structural beams further include a blunt face connected to the at least one surface. As an example, the plurality of structural beams have an axial cross-section in the shape of a triangle.

In at least one embodiment, one or more substrates are coupled to the one or more grids. The one or more substrates are substantially transparent to the UV light.

In at least one embodiment, the one or more grids include an interior grid, and an exterior grid. As an example, the exterior grid is staggered in relation to the interior grid, and vice versa. For example, the beams of the interior grid are closer to a longitudinal axis of the UV light source than the beams of the exterior grid. In at least one example, the beams of the exterior grid are not directly over or under the beams of the interior grid. As an example, the beams of the exterior grid are in a shadow formed by the beams of the interior grid as the UV light source emits the UV light.

In at least one embodiment, the plurality of light openings are sized based on a frequency of the UV light emitted from the UV light source.

Certain embodiments of the present disclosure provide an electromagnetic interference (EMI) reducing cover configured to couple to a housing of a UV lamp assembly having a UV light source that is configured to emit UV light through a light outlet of the housing. The EMI reducing cover includes one or more grids including a plurality of structural beams that define a plurality of light openings. The plurality of light openings facilitate passage of the UV light emitted from the UV light source. The beams include at least one surface that is transverse to a direction of the UV light that is to be emitted from the UV light source.

Certain embodiments of the present disclosure provide an electromagnetic interference (EMI) reducing cover configured to couple to a housing of a UV lamp assembly having a UV light source that is configured to emit UV light through a light outlet of the housing. The EMI reducing cover includes an interior grid, and an exterior grid. The interior grid and the exterior grid include a plurality of structural beams that define a plurality of light openings. The plurality of light openings facilitate passage of the UV light emitted from the UV light source.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

As described herein, embodiments of the present disclosure provide an EMI reducing cover for a UV lamp assembly. The EMI reducing cover mounts to the UV lamp assembly. For example, the EMI reducing cover mounts to a housing that contains one or more UV light emitters. In at least one embodiment, the EMI reducing cover is not directly mounted or otherwise secured to the UV light emitter(s). The EMI reducing cover includes a plurality of intersecting beams that form a grid that is as open as possible, and is configured to suppress EMI generated by the UV light emitter(s) and also maximize or otherwise increase an amount of UV light passing out of a window of the UV lamp assembly (in contrast to being reflected back toward the UV light emitter(s)).

Certain embodiments of the present disclosure provide a UV light sanitizing system including an EMI reducing cover secured to a housing of a UV lamp assembly. The EMI reducing cover includes one or more metallic EMI grids, which are sized and shaped to maximize or otherwise increase passage of UV light and minimize or otherwise reduce EMI. The grid(s) includes a plurality of intersecting beams (such as ribs, wires, or the like). The beams are relatively thin and spaced apart from each other. In at least one embodiment, the ribs have a triangular cross sectional area having two transverse faces faced toward the light source to facilitate reflection of light outwardly to a target disinfection area. The EMI reducing cover can be formed from a reflective materials, such as a metal, such as Copper or Aluminum. In at least one other embodiment, the EMI reducing cover include two more grids stacked and staggered such that an outer grid is in the shadow of an inner grid.

Certain embodiments of the present disclosure provide a method of making an EMI reducing cover. The method includes angling a water jet device in relation to a rib to form a surface that reflects UV light away from a UV light source.

Embodiments of the present disclosure provide an EMI grid that reduces (for example, suppresses) EMI generated by a UV light source, while increasing UV light irradiance through the EMI reducing cover for effective disinfection of a target area/surface with a recued amount of power.

Figure 1:
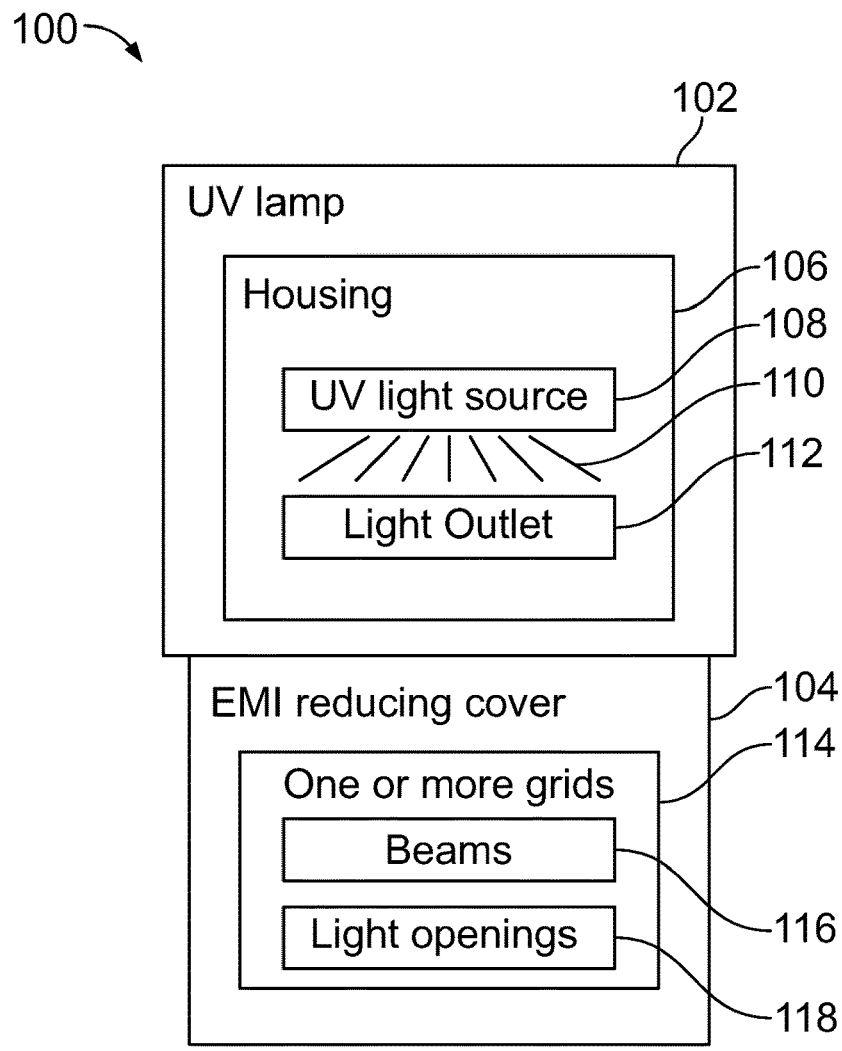
FIG. 1 illustrates a schematic block diagram of a UV light sanitizing system, according to an embodiment of the present disclosure.

FIG. 1 illustrates a schematic block diagram of a UV light sanitizing system 100, according to an embodiment of the present disclosure. The UV light sanitizing system 100 is configured to sanitize one or more portions (such as surfaces, fluid such as air, or the like) of an environment. The environment can be an internal cabin of a vehicle, such as an aircraft. The UV light sanitizing system 100 can be used with various other environments, such as enclosed spaces (such as within residential or commercial buildings), open air venues (such as stadiums), and/or the like.

The UV light sanitizing system 100 includes a UV lamp assembly 102 and an electromagnetic interference (EMI) reducing cover 104 coupled to the UV lamp assembly 102. The UV lamp assembly 102 includes a housing 106 that retains a UV light source 108 that is configured to emit UV light 110 out of a light outlet 112. For example, the UV light source 108 is or otherwise includes one or more UV light emitters, such as UV light bulbs, such as excimer bulbs, UV light emitting diode(s) (LEDs), and/or the like. The light outlet 112 is or otherwise includes an opening, window (such as an open outlet or UV transparent glass panel), and/or the like.

In at least one embodiment, the UV light source 108 includes one or more UV light emitters, such as may include one or more electrodes. The UV light source 108 can also include a transparent (such as a glass) housing surrounding the electrode(s). The UV light source 108 can also include a grid or the like surrounding and/or embedded in the transparent housing.

The EMI reducing cover 104 is coupled to the housing 106 and is disposed within and/or over at least a portion of the light outlet 112. For example, the EMI reducing cover 104 spans across and over the light outlet 112. As another example, the EMI reducing cover 104 is disposed within, over and/or below the light outlet 112. The EMI reducing cover 104 can be secured to an outer circumference, edge, or the like of the housing 106 that defines at least a portion of the light outlet 112. In at least one embodiment, the EMI reducing cover 104 is not directly secured or otherwise coupled to the UV light source 108.

The EMI reducing cover 104 includes one or more grids 114. The grid(s) 114 include a plurality of structural beams 116, such as a mesh of intersecting beams 116. Examples of the beams 116 include ribs, wires, or the like. A plurality of light openings 118 are defined between the beams 116. The light openings 118 provide open areas through which the UV light emitted from the UV light source 108 passes.

In at least one embodiment, the EMI reducing cover 104 can be a mesh screen including a plurality of longitudinal beams 116 that intersect a plurality of orthogonal cross beams 116, thereby forming the plurality of light openings 118 therebetween. In at least one embodiment, the EMI reducing cover 104 is a stamped, water jet cut, or laser cut metal sheet (such as formed of Aluminum, Copper, or stainless steel) with formed apertures (that is, the light openings 118). Aluminum, for example, is approximately 65% reflective of UV light having a wavelength of 222 nanometers (nm). Copper, for example, is approximately 60% of UV light having a wavelength of 222 nm.

In operation, the EMI reducing cover 104 reduces EMI generated by the UV light source 108, while allowing the UV light 110 emitted from the UV light source 108 to pass through the light outlet 112 and the light openings 118 away from the UV light source 108. That is, the light openings 118 allow the UV light to pass out of the UV light sanitizing system 100, while the beams 116 are sized and shaped to minimize or otherwise reduce reflection of UV light 110 back toward the UV light source 108.

In at least one embodiment, the EMI reducing cover 104 includes at least 90% open space relative to the plurality of structural beams 116. That is, the light openings 118 provide at least 90% of the EMI reducing cover 104, while the structural beams 116 provide 10% or less of the EMI reducing cover 104. As a further example, the light openings 118 form at least 94% of the EMI reducing cover 104.

The UV light source 108 can be configured to emit the UV light 110 within the far UV light spectrum, such as at 222 nm. As another example, the UV light source 108 can be configured to emit the UV light 110 within the UVC spectrum, such as at 254 nm. Optionally, the UV light source 108 can be configured to emit the UV light 110 at other wavelengths.

The UV lamp assembly 102 can be fixed in position. For example, the UV lamp assembly 102 can be secured and fixed to a wall, ceiling, cabinet, or the like. Optionally, the UV lamp assembly 102 can be mobile. For example, the lamp 102 can be secured to a structure, and configured to pivot, rotate, articulate, and/or the like. As another example, the UV lamp assembly 102 can be part of a portable device, such as contained within a wand assembly, such as can be coupled to a backpack assembly, a case assembly, a cart assembly, or the like.

Figure 2:
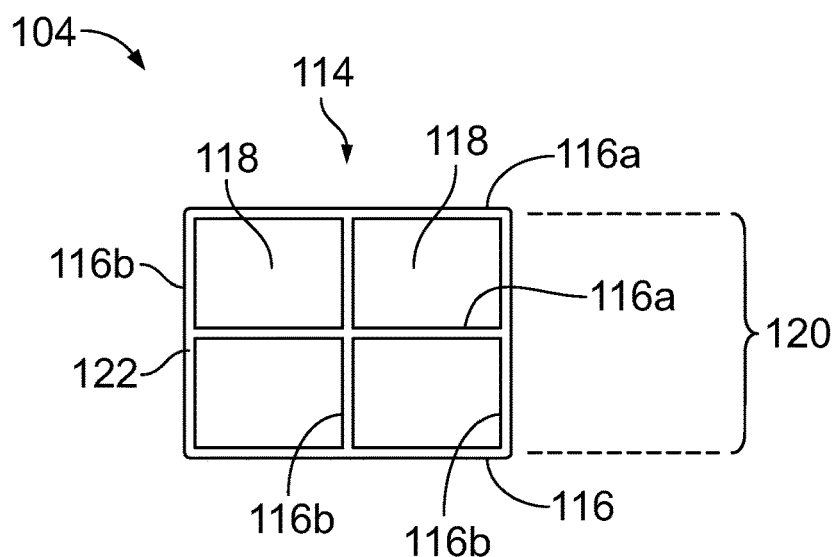
FIG. 2 illustrates a plan view of a portion of an EMI reducing cover, according to an embodiment of the present disclosure.

FIG. 2 illustrates a plan view of a portion of the EMI reducing cover 104, according to an embodiment of the present disclosure. Referring to FIGS. 1 and 2, in at least one embodiment, the EMI reducing cover 104 includes a grid 114 having a plurality of beams 116a (such as cross beam) that intersect a plurality of orthogonal beams 116b, thereby forming a plurality of light openings 118 therebetween. A pitch 120 of the EMI reducing cover 104 is defined between three beams 116a and three beams 116b.

In at least one embodiment, the pitch 120 for the EMI reducing cover 104 is 0.3" (inches) or less. For example, the pitch 120 is 0.2935". The thickness 122 of each beam 116a and 116b is less than 0.02". For example, the thickness is 0.01". Accordingly, the EMI grid 104 is over 90% open. That is, the light openings 118 provide at least 90% of the EMI grid 104. For example, the EMI grid 104 is at least 94% open.

It is to be understood that the examples for the pitch 120 and the thickness 122 are merely exemplary. The pitch 120 can be greater or less than 0.3" and the thickness 122 can be greater or less than 0.02".

In at least one embodiment, the ratio of the pitch 120 to the thickness 122 of the beams 116a and 116b is 15:1. As a further example, the ratio of the pitch 120 to the thickness 122 of the beams 116a and 116b is 30:1. As a still further example, the ratio of the pitch 120 is 29.35:1. It has been found that the EMI reducing cover 104 having a pitch of 0.2935" with the beams 116a and 116b having a thickness 122 of 0.01" increases UV light transmission through the resulting light openings 118 at least 15% over a grid having beam thickness of 0.3", while at the same time suppressing EMI generated by the UV light source 108.

It has been found that embodiments of the present disclosure including the EMI reducing cover 104 having the beams 116, which are sized and shaped as described herein, exceed requirements for EMI, as dictated by Federal Aviation Administration (FAA) requirements. That is, the EMI reducing cover 104 having the ratio of pitch 120 to thickness 122 as described herein suppresses sufficient EMI to be below an upper limit of such requirements.

Additionally, the EMI reducing cover 104 provides a barrier that safely protects the UV light source 108. The EMI reducing cover 104 is interposed between the UV light source 108 and external forces (such as an individual grasping the system 100), and therefore prevents or otherwise reduces a potential of damage to the UV light source 108. Further, the EMI reducing cover 104 provides a barrier against the UV light source 108 being touched (for example, finger oils can absorb 222 nm light).

In at least one embodiment, the plurality of light openings 118 are sized based on a frequency of the UV light 110 emitted from the UV light source 108. For example, the light openings 118 can be sized and shaped to allow for passage of the UV light 110 in the far UV spectrum, such as at 222 nm. As another example, the light openings 118 can be sized and shaped to allow for passage of the UV light 110 in the UVC spectrum, such as at 254 nm. As an example, the beams 116 may be sized and shaped to suppress EMI having a first wavelength, but allow for increased passage of UV light at a second wavelength, which is less than the first wavelength.

Figure 3:
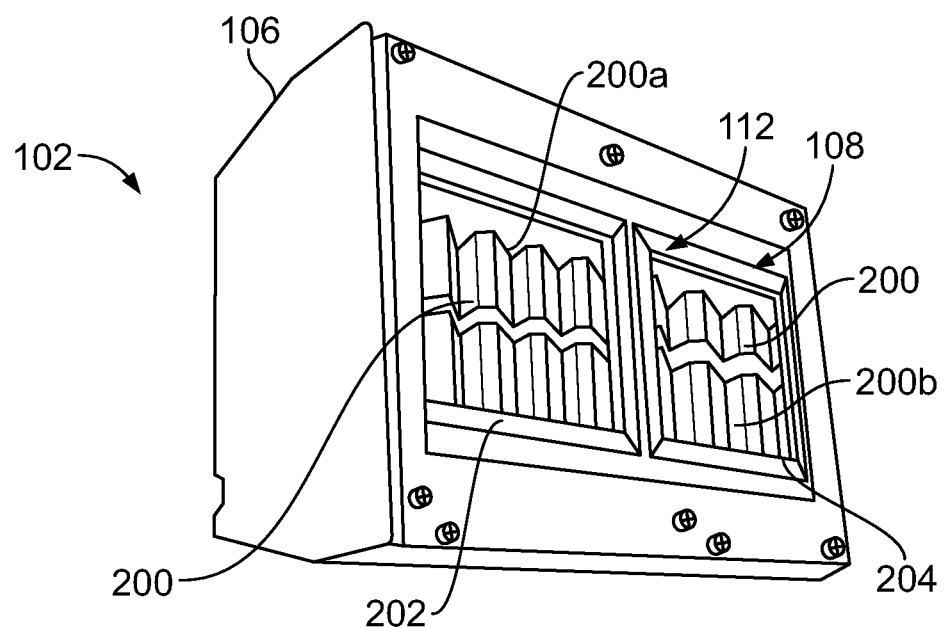
FIG. 3 illustrates a perspective view of a first side of a UV lamp assembly, according to an embodiment of the present disclosure.

FIG. 3 illustrates a perspective view of a first side (such as a bottom or top) of a UV lamp assembly 102, according to an embodiment of the present disclosure. The UV lamp assembly 102 includes the housing 106 that retains the UV light source 108, such as plurality of UV light emitters 200 that are configured to emit UV light through the light outlet 112, such as an aperture. As shown, the UV lamp assembly 102 includes a first plurality of UV light emitters 200a and a second plurality of UV light emitters 200b. The first plurality of UV light emitters 200a are contained within a first sub-housing 202, and the second plurality of UV light emitters 200b are contained within a second sub-housing 204 that is distinct from the first sub-housing 202. Each of the first sub-housing 202 and the second sub-housing 204 can contain more or less UV light emitters 200 than shown. Optionally, the UV lamp assembly 102 can include a single sub-housing that retains all of the UV light emitters 200. In at least one embodiment, the UV lamp assembly 102 can include a single UV light emitter 200, instead a plurality of UV light emitters 200. The UV lamp assembly 102 shown in FIG. 3 is merely an example. The UV lamp assembly 102 can be sized and shaped differently than shown in FIG. 3.

Figure 4:
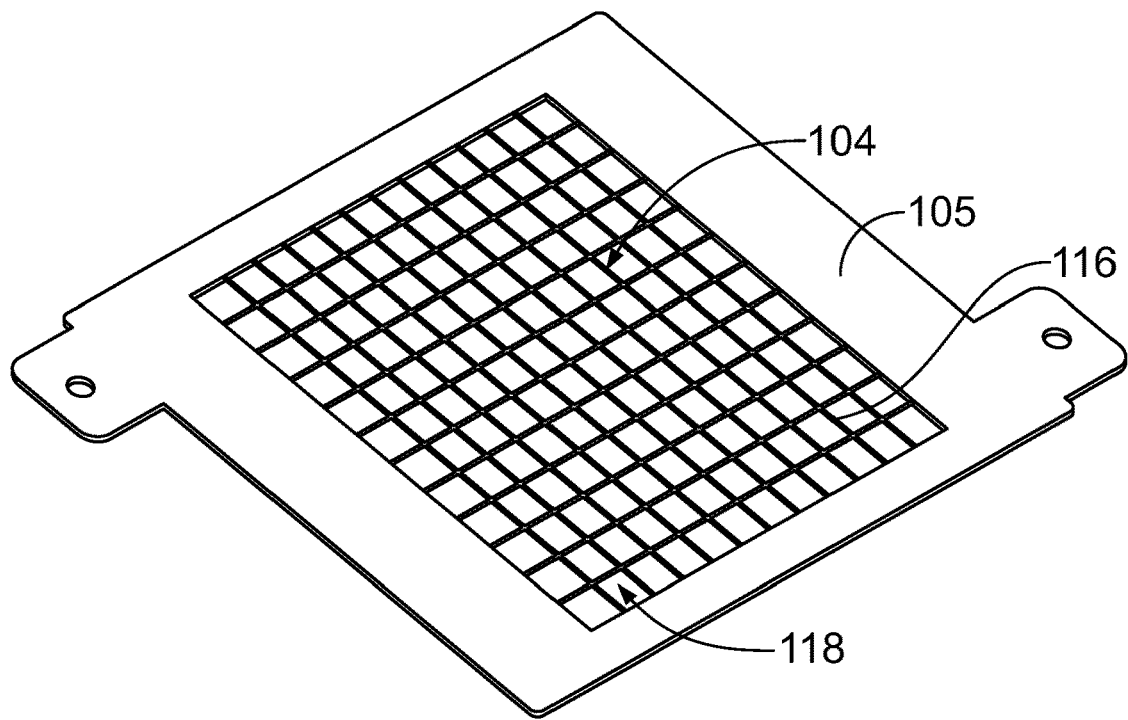
FIG. 4 illustrates a top view of an EMI reducing cover, according to an embodiment of the present disclosure.
Figure 5:
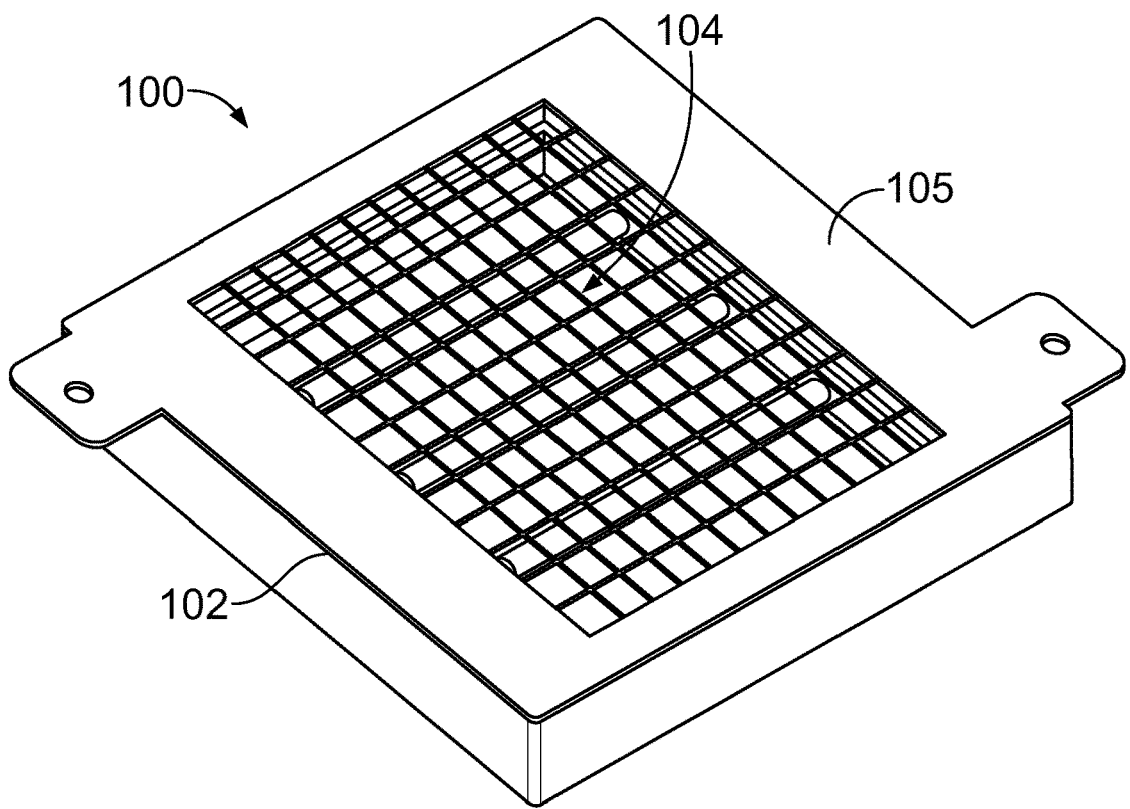
FIG. 5 illustrates a perspective view of a UV light sanitizing system, according to an embodiment of the present disclosure.

FIG. 4 illustrates a top view of the EMI reducing cover 104, according to an embodiment of the present disclosure. FIG. 5 illustrates a perspective view of the UV light sanitizing system 100, according to an embodiment of the present disclosure. Referring to FIGS. 1-5, in at least one embodiment, the EMI reducing cover 104 includes an outer frame 105. The beams 116 and light openings 118 are disposed inboard from the outer frame 105. The outer frame 105 is configured to be secured to the housing 106, such as proximate to the light outlet 112.

Figure 6:
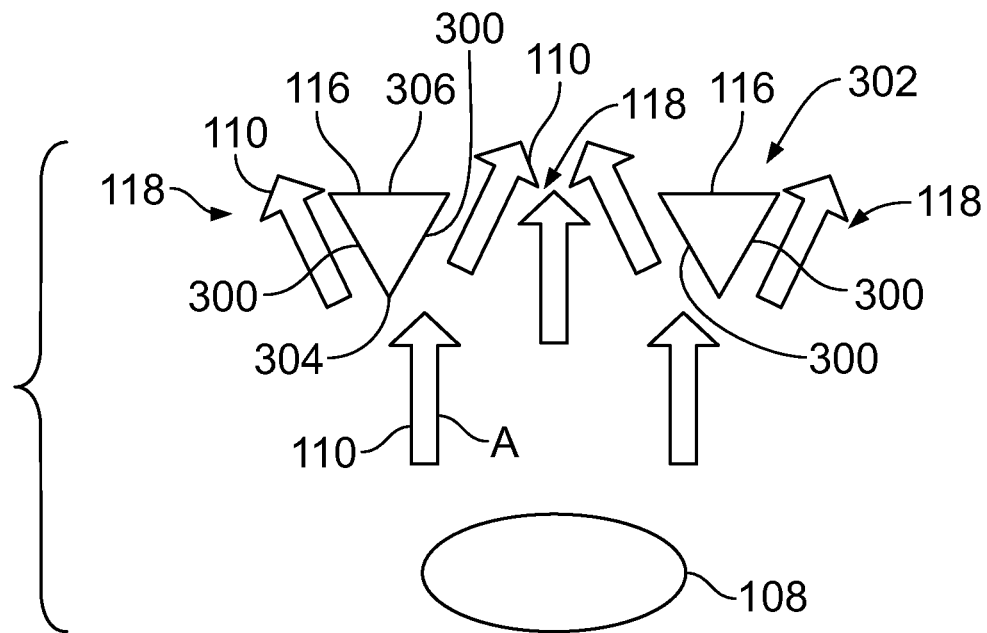
FIG. 6 illustrates axial cross-sectional views of beams of the EMI reducing cover, according to an embodiment of the present disclosure.

FIG. 6 illustrates axial cross-sectional views of beams 116 of the EMI reducing cover 104, according to an embodiment of the present disclosure. As shown, the beams 116 may be shaped having at least one surface 300 that is transverse to a direction A of the UV light 110 emitted from the UV light source 108. For example, the beams 116 may have an axial cross-section in the shape of a triangle 302, in which two sides have the surfaces 300 that meet at an apex 304 closest to the UV light source 108. A distal side 306 is away from the apex 304 and the UV light source 108. The distal side 306 can be perpendicular to the direction A, whereas the surfaces 300 that form the other sides are non-perpendicular to the direction A.

In at least one embodiment, at least one surface 300 is configured to face the UV light source 108. The surface(s) 300 includes a reflective material that facilitates reflecting at least some of the UV light 110 through the one or more light openings 118. As shown in FIG. 6, for example, two surfaces 300 are transverse to the direction A of the UV light 110 that is to be emitted from the UV light source 108.

The UV light 110 is reflected off the surfaces 300 away from the UV light source 108. In this manner, the UV light 110 is not reflected back toward the UV light source 108. The angled faces of the surfaces 300 reflect the UV light 110 emitted from the UV light source 108 into the light openings 118, instead of back toward the UV light source 108.

As shown, the beams 116 can be shaped having an axial cross-section in the form of an equilateral triangle. Optionally, the beams 116 can be shaped having an axial cross-section in the form of a right triangle. As another example, the beams 116 can be shaped having an axial cross-section in the form of an isosceles triangle. As another example, the beams 116 can be shaped having an axial cross-section in the form of a trapezoid, or another shape having at least one surface 300 that is transverse to the direction A (and non-perpendicular to the direction A).

An EMI reducing cover 104 having beams 116 as shaped as shown and described with respect to FIG. 6 allows more UV light reflections into the light openings 118. Further, such an EMI reducing cover 104 is more robust than a grid that has ultra-thin ribs. Further, the flat side 306 provides a blunt face. As such, the exposed blunt face is unlikely to cut an individual who touches it, in contrast to grasping a very thin face, which may be sharp.

In at least one embodiment, the beams 116 are sized and spaced in relation to the EMI reducing cover 104 as described with respect to FIGS. 1 and 2. Optionally, the beams 116 can be sized and spaced differently than as described with respect to FIGS. 1 and 2.

Figure 7:
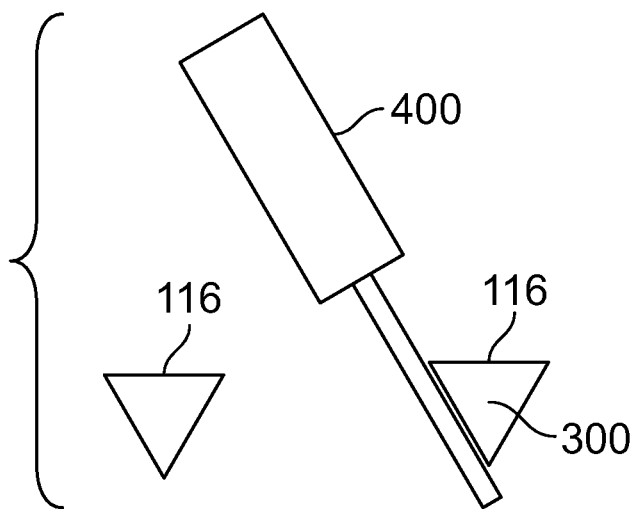
FIG. 7 illustrates a lateral view of a device forming a surface of a beam of the EMI reducing cover, according to an embodiment of the present disclosure.

FIG. 7 illustrates a lateral view of a device 400 forming a surface of a beam of the EMI reducing cover, according to an embodiment of the present disclosure. The device 400 can be a laser that emits laser energy onto the beam 116 to form the surface 300. As another example, the device 400 can be a water jet that emits pressurized water onto the beam 116 to form the surface 300.

The shape of the beams 116 is created by angling the device 400 during each cut of the beams 116. For example, the device 400 provides angled surfaces on a metal substrate, such as formed of Aluminum or Copper.

Figure 8:
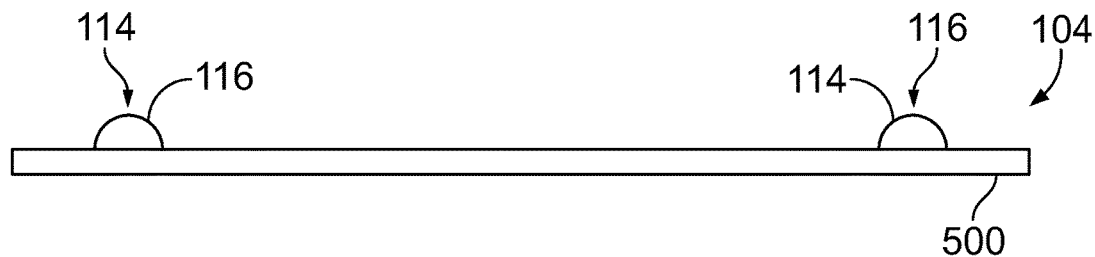
FIG. 8 illustrates an end view of an EMI reducing cover, according to an embodiment of the present disclosure.

FIG. 8 illustrates an end view of the EMI reducing cover 104, according to an embodiment of the present disclosure. In this embodiment, a grid 114 including beams 116 is supported on a substrate 500. The substrate 500 is transparent or substantially transparent to UV light. For example, the substrate 500 is a panel of glass, which is 99.95% transparent to UV light.

The grid 114 can be bonded to the substrate 500. As another example, the grid 114 can be printed on the substrate 500. As another example, the grid 114 can be etched onto the substrate 500. As another example, the grid 114 can be deposited onto the substrate 500.

Figure 9:
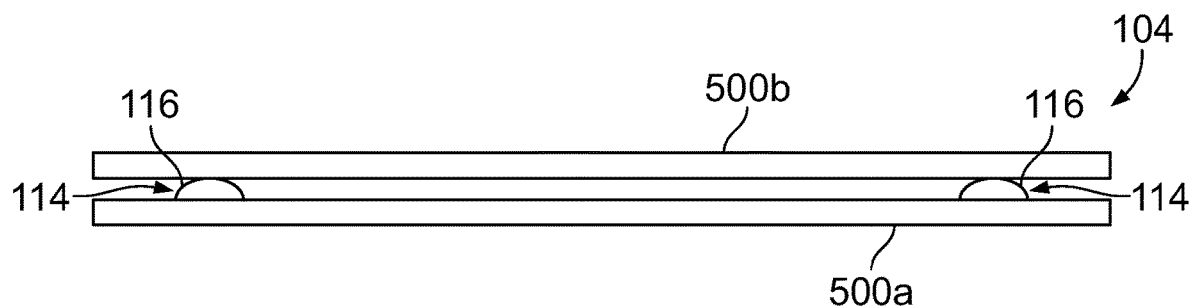
FIG. 9 illustrates an end view of an EMI reducing cover, according to an embodiment of the present disclosure.

FIG. 9 illustrates an end view of an EMI reducing cover 104, according to an embodiment of the present disclosure. In this embodiment, the grid 114 is sandwiched between a first substrate 500a and a second substrate 500b.

Referring to FIGS. 8 and 9, the substrate(s) 500 provide structural support and rigidity to the EMI reducing cover 104. Optionally, the EMI reducing cover 104 may not include any substrates.

In at least one embodiment, the beams 116 are sized and spaced in relation to the EMI reducing cover 104 as described with respect to FIGS. 1 and 2. Optionally, the beams 116 can be sized and spaced differently than as described with respect to FIGS. 1 and 2.

Figure 10:
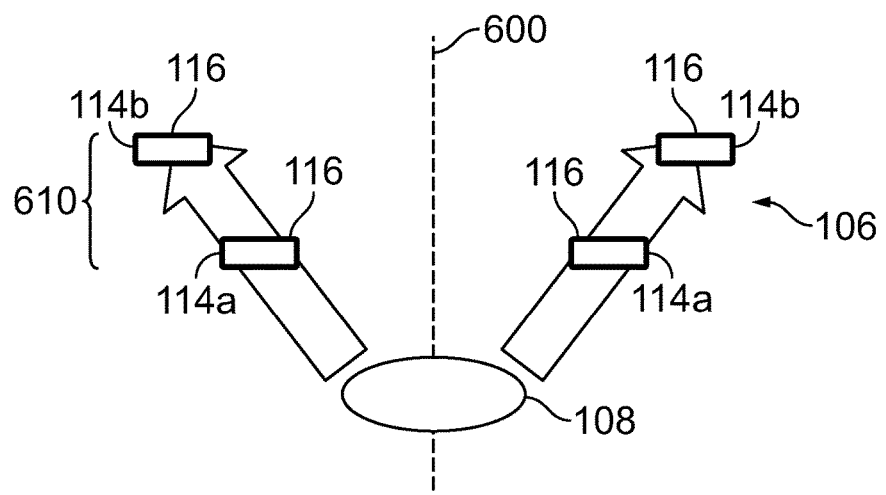

FIG. 10 illustrates axial cross-sectional views of beams of the EMI reducing cover 104, according to an embodiment of the present disclosure. In at least one embodiment, the EMI reducing cover 104 includes an interior grid 114a of beams 116, and an exterior grid 114b of beams 116. The beams 116 can be sized, shaped, and configured, as described with respect to FIGS. 1-9.

The interior grid 114a is closer to the UV light source 108 than the exterior grid 114b. The beams 116 of the interior grid 114a are staggered in relation to the beams 116 of the exterior grid 114b, and vice versa. For example, the beams 116 of the interior grid 114a are closer to a longitudinal axis 600 of the UV light source 108 than the beams 116 of the exterior grid 114b. The beams 116 of the exterior grid 114b are not directly over or under the beams 116 of the interior grid 114a. Instead, the beams 116 of the exterior grid 114b are radially further outward than the beams 116 of the interior grid 114a. In at least one embodiment, the beams 116 of the exterior grid 114b are in a shadow formed by the beams 116 of the interior grid 114a as the UV light source 108 emits the UV light 110.

In at least one embodiment, the beams 116 are sized and spaced in relation to the EMI reducing cover 104 as described with respect to FIGS. 1 and 2. Optionally, the beams 116 can be sized and spaced differently than as described with respect to FIGS. 1 and 2.

The interior grid 114a is spaced apart from the exterior grid 114a a distance 610. For example, the distance 610 can be 0.001"-0.25". Optionally, the distance can be less than 0.001" or greater than 0.25".

The light openings 118 between the beams 116 of the exterior grid 114b and the beams 116 of the interior grid 114a can be sized and shaped based on a frequency or wavelength of the UV light emitted 110 emitted from the UV light source 108. For example, the light openings 118 can be sized and shaped to allow for passage of the UV light 110 in the far UV spectrum, such as at 222 nm. As another example, the light openings 118 can be sized and shaped to allow for passage of the UV light 110 in the UVC spectrum, such as at 254 nm. As an example, the beams 116 may be sized and shaped to suppress EMI having a first wavelength, but allow for increased passage of UV light at a second wavelength, which is less than the first wavelength.

Figure 11:
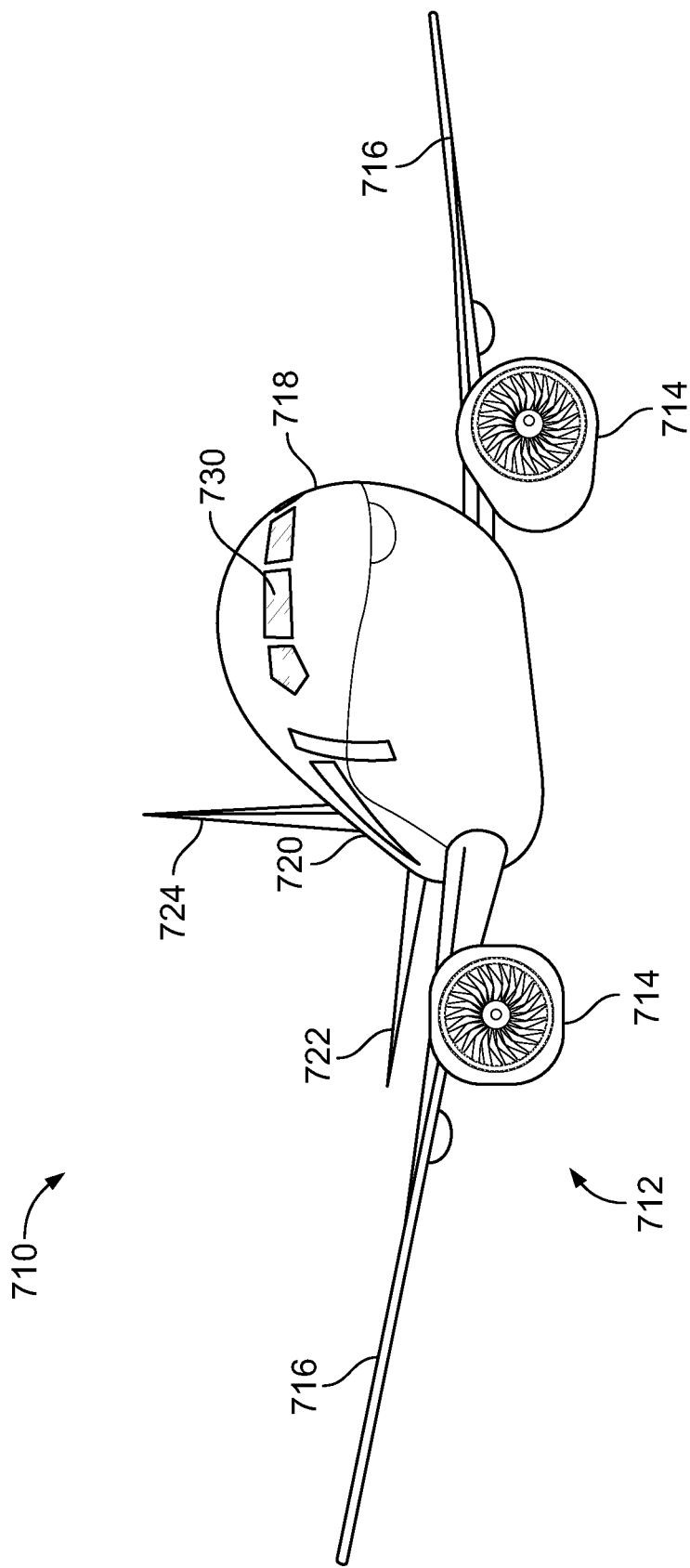
FIG. 11 illustrates a perspective front view of an aircraft, according to an embodiment of the present disclosure.

FIG. 11 illustrates a perspective front view of an aircraft 710, according to an embodiment of the present disclosure. The aircraft 710 includes a propulsion system 712 that includes engines 714, for example. Optionally, the propulsion system 712 may include more engines 714 than shown. The engines 714 are carried by wings 716 of the aircraft 710. In other embodiments, the engines 714 may be carried by a fuselage 718 and/or an empennage 720. The empennage 720 may also support horizontal stabilizers 722 and a vertical stabilizer 724.

The fuselage 718 of the aircraft 710 defines an internal cabin 730, which includes a flight deck or cockpit, one or more work sections (for example, galleys, personnel carry-on baggage areas, and the like), one or more passenger sections (for example, first class, business class, and coach sections), one or more lavatories, and/or the like.

Embodiments of the present disclosure, as shown and described with respect to FIGS. 1-10, can be used within the internal cabin of the aircraft 710, for example. Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 12A:
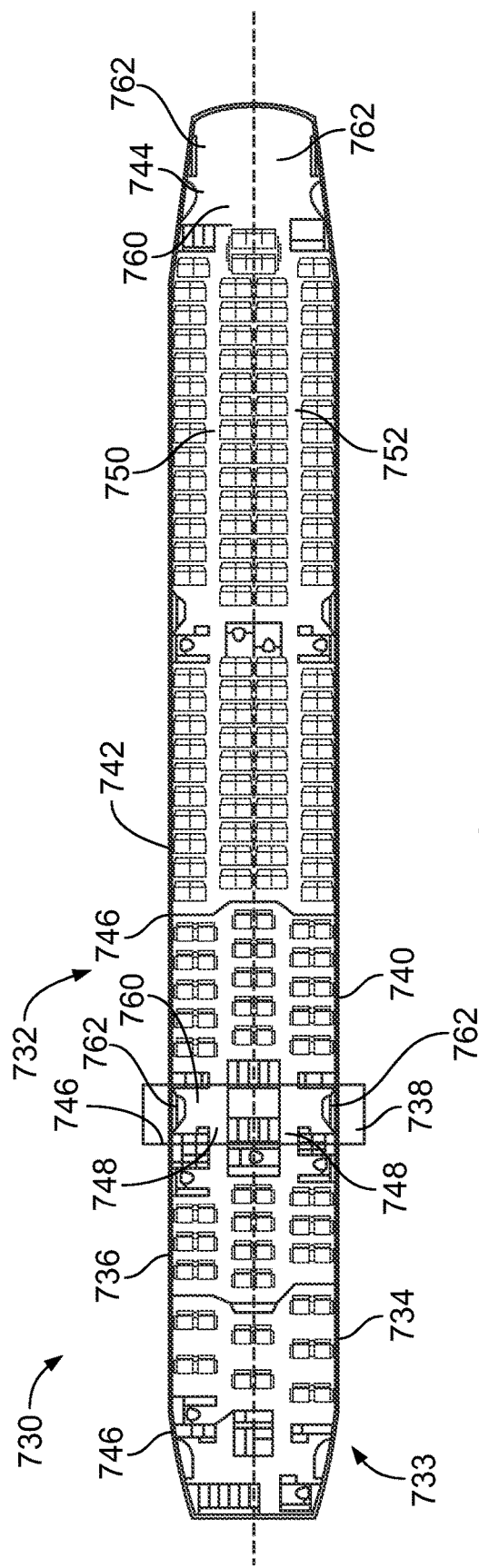
FIG. 12A illustrates a top plan view of an internal cabin of an aircraft, according to an embodiment of the present disclosure.

FIG. 12A illustrates a top plan view of an internal cabin 730 of an aircraft, according to an embodiment of the present disclosure. The internal cabin 730 may be within the fuselage 732 of the aircraft, such as the fuselage 718 of FIG. 11. For example, one or more fuselage walls may define the internal cabin 730. The internal cabin 730 includes multiple sections, including a front section 733, a first class section 734, a business class section 736, a front galley station 738, an expanded economy or coach section 740, a standard economy of coach section 742, and an aft section 744, which may include multiple lavatories and galley stations. It is to be understood that the internal cabin 730 may include more or less sections than shown. For example, the internal cabin 730 may not include a first class section, and may include more or less galley stations than shown. Each of the sections may be separated by a cabin transition area 746, which may include class divider assemblies between aisles 748.

As shown in FIG. 12A, the internal cabin 730 includes two aisles 750 and 752 that lead to the aft section 744. Optionally, the internal cabin 730 may have less or more aisles than shown. For example, the internal cabin 730 may include a single aisle that extends through the center of the internal cabin 730 that leads to the aft section 744.

The aisles 748, 750, and 752 extend to egress paths or door passageways 760. Exit doors 762 are located at ends of the egress paths 760. The egress paths 760 may be perpendicular to the aisles 748, 750, and 752. The internal cabin 730 may include more egress paths 760 at different locations than shown. Embodiments of the present disclosure shown and described with respect to FIGS. 1-10 may be used within the internal cabin 730.

Figure 12B:
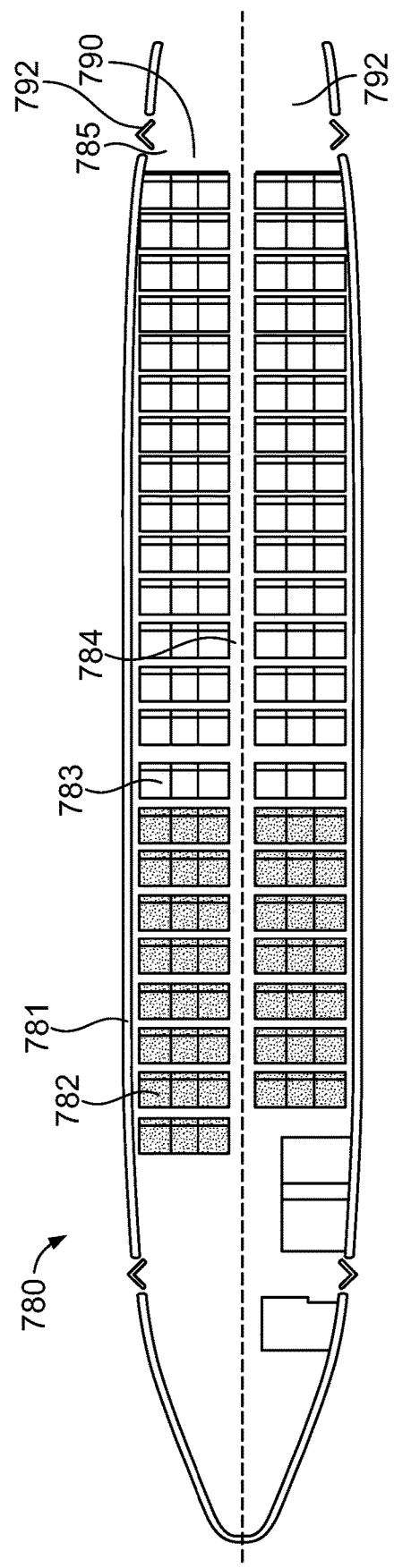
FIG. 12B illustrates a top plan view of an internal cabin of an aircraft, according to an embodiment of the present disclosure.

FIG. 12B illustrates a top plan view of an internal cabin 780 of an aircraft, according to an embodiment of the present disclosure. The internal cabin 780 is an example of the internal cabin 730 shown in FIG. 11. The internal cabin 780 may be within a fuselage 781 of the aircraft. For example, one or more fuselage walls may define the internal cabin 780. The internal cabin 780 includes multiple sections, including a main cabin 782 having passenger seats 783, and an aft section 785 behind the main cabin 782. It is to be understood that the internal cabin 780 may include more or less sections than shown.

The internal cabin 780 may include a single aisle 784 that leads to the aft section 785. The single aisle 784 may extend through the center of the internal cabin 780 that leads to the aft section 785. For example, the single aisle 784 may be coaxially aligned with a central longitudinal plane of the internal cabin 780.

The aisle 784 extends to an egress path or door passageway 790. Exit doors 792 are located at ends of the egress path 790. The egress path 790 may be perpendicular to the aisle 784. The internal cabin 780 may include more egress paths than shown. Embodiments of the present disclosure shown and described with respect to FIGS. 1-10 may be used within the internal cabin 780.

Figure 13:
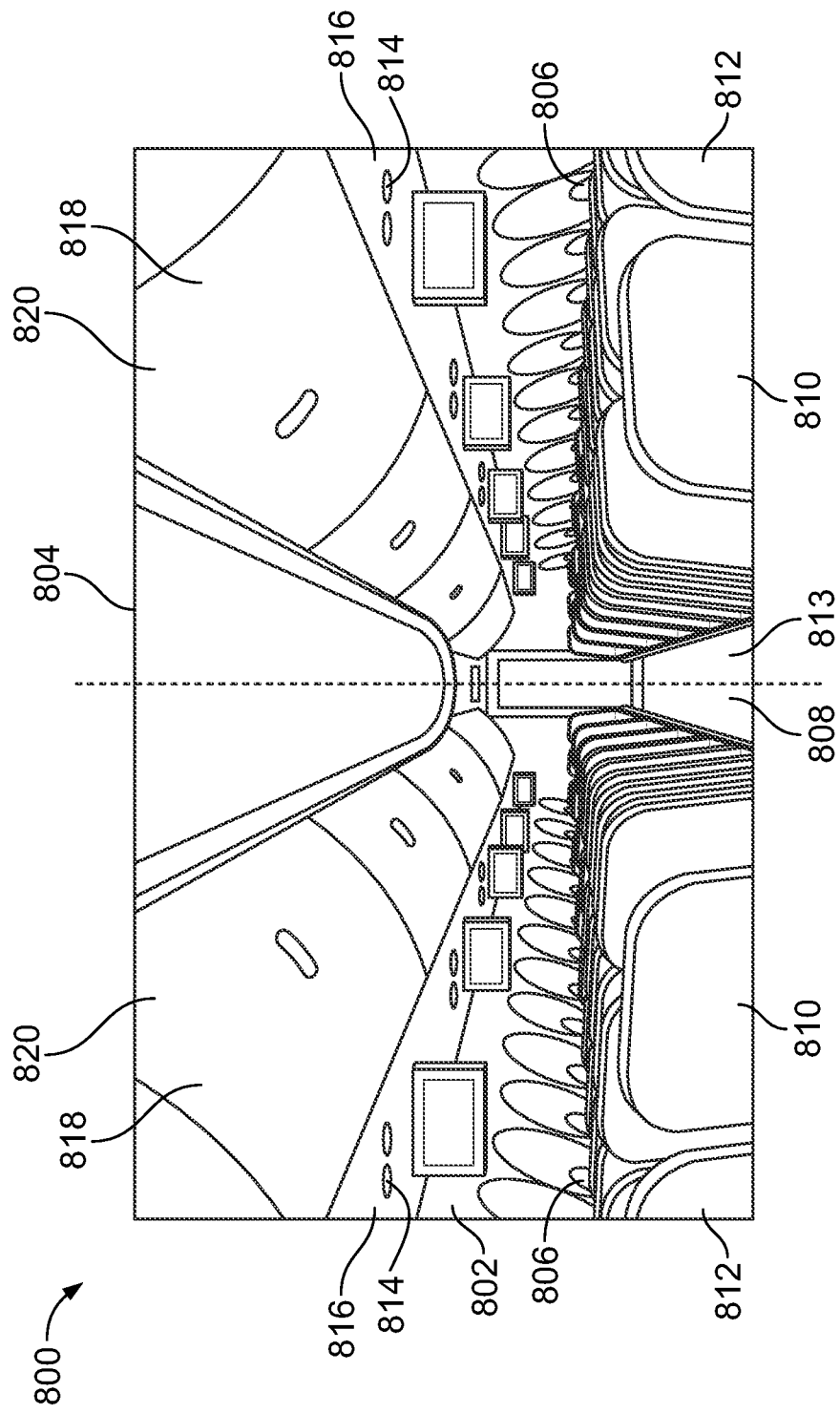
FIG. 13 illustrates a perspective interior view of an internal cabin of an aircraft, according to an embodiment of the present disclosure.

FIG. 13 illustrates a perspective interior view of an internal cabin 800 of an aircraft, according to an embodiment of the present disclosure. The internal cabin 800 includes outboard walls 802 connected to a ceiling 804. Windows 806 may be formed within the outboard walls 802. A floor 808 supports rows of seats 810. As shown in FIG. 13, a row 812 may include two seats 810 on either side of an aisle 813. However, the row 812 may include more or less seats 810 than shown. Additionally, the internal cabin 800 may include more aisles than shown.

Passenger service units (PSUs) 814 are secured between an outboard wall 802 and the ceiling 804 on either side of the aisle 813. The PSUs 814 extend between a front end and rear end of the internal cabin 800. For example, a PSU 814 may be positioned over each seat 810 within a row 812. Each PSU 814 may include a housing 816 that generally contains vents, reading lights, an oxygen bag drop panel, an attendant request button, and other such controls over each seat 810 (or groups of seats) within a row 812.

Overhead stowage bin assemblies 818 are secured to the ceiling 804 and/or the outboard wall 802 above and inboard from the PSU 814 on either side of the aisle 813. The overhead stowage bin assemblies 818 are secured over the seats 810. The overhead stowage bin assemblies 818 extend between the front and rear end of the internal cabin 800. Each stowage bin assembly 818 may include a pivot bin or bucket 820 pivotally secured to a strongback (hidden from view in FIG. 13). The overhead stowage bin assemblies 818 may be positioned above and inboard from lower surfaces of the PSUs 814. The overhead stowage bin assemblies 818 are configured to be pivoted open in order to receive passenger carry-on baggage and personal items, for example.

Embodiments of the present disclosure shown and described with respect to FIGS. 1-10 can be used in the internal cabin 800.

Further, the disclosure comprises embodiments according to the following clauses:

Clause 1. An electromagnetic interference (EMI) reducing cover configured to couple to a housing of a UV lamp assembly having a UV light source that is configured to emit UV light through a light outlet of the housing, the EMI reducing cover comprising:

one or more grids comprising a plurality of structural beams that define a plurality of light openings, wherein the plurality of light openings facilitate passage of the UV light emitted from the UV light source, and wherein the EMI reducing cover includes at least 90 percent open space relative to the plurality of the plurality of structural beams.

Clause 2. The EMI reducing cover of Clause 1, wherein the EMI reducing cover is not configured to be directly coupled to the UV light source.

Clause 3. The EMI reducing cover of Clauses 1 or 2, wherein the plurality of structural beams are formed of a reflective material.

Clause 4. The EMI reducing cover of any of Clauses 1-3, wherein a pitch of the EMI reducing cover is 0.3 inches or less, and wherein a thickness of each of the beams is 0.02 inches or less.

Clause 5. The EMI reducing cover of any of Clauses 1-4, wherein a pitch of the EMI reducing cover is 0.2935 inches, and wherein a thickness of each of the beam is 0.01 inches.

Clause 6. The EMI reducing cover of any of Clauses 1-5, wherein a ratio of a pitch of the EMI reducing cover to a thickness of each of the beams is at least 15:1.

Clause 7. The EMI reducing cover of any of Clauses 1-6, wherein a ratio of a pitch of the EMI reducing cover to a thickness of each of the beams is 29.35:1.

Clause 8. The EMI reducing cover of any of Clauses 1-7, wherein a ratio of a pitch of the EMI reducing cover to a thickness of each of the beams is 30:1.

Clause 9. The EMI reducing cover of any of Clauses 1-8, wherein the EMI reducing cover further comprises an outer frame, wherein the plurality of structural beams and the plurality of light openings are disposed inboard from the outer frame, wherein the outer frame is configured to be secured to the housing.

Clause 10. The EMI reducing cover of any of Clauses 1-9, wherein the beams comprise at least one surface that is transverse to a direction of the UV light that is to be emitted from the UV light source.

Clause 11. The EMI reducing cover of Clause 10, wherein the at least one surface is configured to face the UV light source, and wherein the at least one surface includes a reflective material that facilitates reflecting at least some of the UV light through the one or more light openings.

Clause 12. The EMI reducing cover of Clause 11, wherein the at least one surface comprises two surfaces that are transverse to the direction of the UV light that is to be emitted from the UV light source.

Clause 13. The EMI reducing cover of Clause 11, wherein the plurality of structural beams further comprise a blunt face connected to the at least one surface.

Clause 14. The EMI reducing cover of any of Clauses 1-13, wherein the plurality of structural beams have an axial cross-section in the shape of a triangle.

Clause 15. The EMI reducing cover of any of Clauses 1-14, further comprising one or more substrates coupled to the one or more grids, wherein the one or more substrates are substantially transparent to the UV light.

Clause 16. The EMI reducing cover of any of Clauses 1-15, wherein the one or more grids comprise:
  an interior grid; and
  an exterior grid.

Clause 17. The EMI reducing cover of Clause 16, wherein the interior grid is staggered in relation to the exterior grid, and vice versa.

Clause 18. The EMI reducing cover of Clauses 16 or 17, wherein the beams of the interior grid are closer to a longitudinal axis of the UV light source than the beams of the exterior grid.

Clause 19. The EMI reducing cover of any of Clauses 16-18, wherein the beams of the exterior grid are not directly over or under the beams of the interior grid.

Clause 20. The EMI reducing cover of any of Clauses 16-19, wherein the beams of the exterior grid are in a shadow formed by the beams of the interior grid as the UV light source emits the UV light.

Clause 21. The EMI reducing cover of any of Clauses 16-20, wherein the plurality of light openings are sized based on a frequency of the UV light emitted from the UV light source.

Clause 22. An electromagnetic interference (EMI) reducing cover configured to couple to a housing of a UV lamp assembly having a UV light source that is configured to emit UV light through a light outlet of the housing, the EMI reducing cover comprising:
  one or more grids comprising a plurality of structural beams that define a plurality of light openings, wherein the plurality of light openings facilitate passage of the UV light emitted from the UV light source, and wherein the beams comprise at least one surface that is transverse to a direction of the UV light that is to be emitted from the UV light source.

Clause 23. The EMI reducing cover of Clause 22, wherein the at least one surface is configured to face the UV light source, and wherein the at least one surface includes a reflective material that facilitates reflecting at least some of the UV light through the one or more light openings.

Clause 24. The EMI reducing cover of Clause 23, wherein the at least one surface comprises two surfaces that are transverse to the direction of the UV light that is to be emitted from the UV light source.

Clause 25. The EMI reducing cover of any of Clauses 22-24, wherein the plurality of structural beams further comprise a blunt face connected to the at least one surface.

Clause 26. The EMI reducing cover of any of Clauses 22-25, wherein the plurality of structural beams have an axial cross-section in the shape of a triangle.

Clause 27. The EMI reducing cover of any of Clauses 22-26, wherein the EMI reducing cover is not configured to directly couple to the UV light source.

Clause 28. The EMI reducing cover of any of Clauses 22-27, wherein the plurality of structural beams are formed of a reflective material.

Clause 29. The EMI reducing cover of any of Clauses 22-28, further comprising an outer frame, wherein the plurality of structural beams and the plurality of light openings are disposed inboard from the outer frame, wherein the outer frame is configured to be secured to the housing.

Clause 30. The EMI reducing cover of any of Clauses 22-29, further comprising one or more substrates coupled to the one or more grids, wherein the one or more substrates are substantially transparent to the UV light.

Clause 31. The EMI reducing cover of any of Clauses 22-30, wherein the one or more grids comprise:
  an interior grid; and
  an exterior grid.

Clause 32. The EMI reducing cover of Clause 31, wherein the interior grid is staggered in relation to the exterior grid, and vice versa.

Clause 33. The EMI reducing cover of Clauses 31 or 32, wherein the beams of the interior grid are closer to a longitudinal axis of the UV light source than the beams of the exterior grid.

Clause 34. The EMI reducing cover of any of Clauses 31-33, wherein the beams of the exterior grid are not directly over or under the beams of the interior grid.

Clause 35. The EMI reducing cover of any of Clauses 31-34, wherein the beams of the exterior grid are in a shadow formed by the beams of the interior grid as the UV light source emits the UV light.

Clause 36. The EMI reducing cover of any of Clauses 22-35, wherein the plurality of light openings are sized based on a frequency of the UV light emitted from the UV light source.

Clause 37. An electromagnetic interference (EMI) reducing cover configured to couple to a housing of a UV lamp assembly having a UV light source that is configured to emit UV light through a light outlet of the housing, the EMI reducing cover comprising:
an interior grid; and
an exterior grid,
wherein the interior grid and the exterior grid comprise a plurality of structural beams that define a plurality of light openings, wherein the plurality of light openings facilitate passage of the UV light emitted from the UV light source.

Clause 38. The EMI reducing cover of Clause 37, wherein the interior grid is staggered in relation to the exterior grid, and vice versa.

Clause 39. The EMI reducing cover of Clauses 37 or 38, wherein the beams of the interior grid are closer to a longitudinal axis of the UV light source than the beams of the exterior grid.

Clause 40. The EMI reducing cover of any of Clauses 37-39, wherein the beams of the exterior grid are not directly over or under the beams of the interior grid.

Clause 41. The EMI reducing cover of any of Clauses 37-40, wherein the beams of the exterior grid are in a shadow formed by the beams of the interior grid as the UV light source emits the UV light.

Clause 42. The EMI reducing cover of any of Clauses 37-41, wherein the EMI reducing cover is not configured to directly couple to the UV light source.

Clause 43. The EMI reducing cover of any of Clauses 37-42, wherein the plurality of structural beams are formed of a reflective material.

Clause 44. The EMI reducing cover of any of clauses 37-43, further comprising an outer frame, wherein the beams and the light openings are disposed inboard from the outer frame, wherein the outer frame is configured to be secured to the housing.

Clause 45. The EMI reducing cover of any of Clauses 37-44, wherein the plurality of light openings are sized based on a frequency of the UV light emitted from the UV light source.

As described herein, embodiments of the present disclosure provide systems and methods for reducing (for example, suppressing) EMI in relation to UV lamp assemblies. Further, embodiments of the present disclosure provide systems and methods for reducing EMI while also allowing passage of a significant amount of UV light (for example, as much UV light as possible) from a UV lamp assembly.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. An electromagnetic interference (EMI) reducing cover configured to couple to a housing of a UV lamp assembly having a UV light source that is configured to emit UV light through a light outlet of the housing, the EMI reducing cover comprising:
one or more grids comprising a plurality of structural beams that define a plurality of light openings, wherein the plurality of structural beams have an axial cross-section in the shape of a triangle, wherein the plurality of light openings facilitate passage of the UV light emitted from the UV light source, and wherein the EMI reducing cover includes at least 90 percent open space relative to the plurality of the plurality of structural beams.

2. The EMI reducing cover of claim 1, wherein the EMI reducing cover is not configured to be directly coupled to the UV light source.

3. The EMI reducing cover of claim 1, wherein the plurality of structural beams are formed of a reflective material.

4. The EMI reducing cover of claim 1, wherein a pitch of the EMI reducing cover is 0.3 inches or less, and wherein a thickness of each of the beams is 0.02 inches or less.

5. The EMI reducing cover of claim 1, wherein a pitch of the EMI reducing cover is 0.2935 inches, and wherein a thickness of each of the beam is 0.01 inches.

6. The EMI reducing cover of claim 1, wherein a ratio of a pitch of the EMI reducing cover to a thickness of each of the beams is at least 15:1.

7. The EMI reducing cover of claim 1, wherein a ratio of a pitch of the EMI reducing cover to a thickness of each of the beams is 29.35:1.

8. The EMI reducing cover of claim 1, wherein a ratio of a pitch of the EMI reducing cover to a thickness of each of the beams is 30:1.

9. The EMI reducing cover of claim 1, wherein the EMI reducing cover further comprises an outer frame, wherein the plurality of structural beams and the plurality of light openings are disposed inboard from the outer frame, wherein the outer frame is configured to be secured to the housing.

10. The EMI reducing cover of claim 1, wherein the beams comprise at least one surface that is transverse to a direction of the UV light that is to be emitted from the UV light source.

11. The EMI reducing cover of claim 10, wherein the at least one surface is configured to face the UV light source, and wherein the at least one surface includes a reflective material that facilitates reflecting at least some of the UV light through the one or more light openings.

12. The EMI reducing cover of claim 11, wherein the at least one surface comprises two surfaces that are transverse to the direction of the UV light that is to be emitted from the UV light source.

13. The EMI reducing cover of claim 11, wherein the plurality of structural beams further comprise a blunt face connected to the at least one surface.

14. The EMI reducing cover of claim 1, further comprising one or more substrates coupled to the one or more grids, wherein the one or more substrates are substantially transparent to the UV light.

15. The EMI reducing cover of claim 1, wherein the one or more grids comprise:
an interior grid; and
an exterior grid.

16. The EMI reducing cover of claim 15, wherein the interior grid is staggered in relation to the exterior grid, and vice versa.

17. The EMI reducing cover of claim 15, wherein the beams of the interior grid are closer to a longitudinal axis of the UV light source than the beams of the exterior grid.

18. The EMI reducing cover of claim 15, wherein the beams of the exterior grid are not directly over or under the beams of the interior grid.

19. The EMI reducing cover of claim 15, wherein the beams of the exterior grid are in a shadow formed by the beams of the interior grid as the UV light source emits the UV light.

20. The EMI reducing cover of claim 1, wherein the plurality of light openings are sized based on a frequency of the UV light emitted from the UV light source.

21. The EMI reducing cover of claim 1, wherein the plurality of structural beams comprise:
a first side;
a second side that meets the first side at an apex, wherein the apex is configured to be proximate to the UV light source; and
a third side opposite from the apex, wherein the third side is configured to be distal from the UV light source.

22. An electromagnetic interference (EMI) reducing cover configured to couple to a housing of a UV lamp assembly having a UV light source that is configured to emit UV light through a light outlet of the housing, the EMI reducing cover comprising:
one or more grids comprising a plurality of structural beams that define a plurality of light openings, wherein the plurality of light openings facilitate passage of the UV light emitted from the UV light source, and wherein the beams comprise at least one surface that is transverse to a direction of the UV light that is to be emitted from the UV light source; and
one or more substrates coupled to the one or more grids, wherein the one or more substrates are substantially transparent to the UV light.

23. An electromagnetic interference (EMI) reducing cover configured to couple to a housing of a UV lamp assembly having a UV light source that is configured to emit UV light through a light outlet of the housing, the EMI reducing cover comprising:
an interior grid; and
an exterior grid,
wherein the interior grid and the exterior grid comprise a plurality of structural beams that define a plurality of light openings, wherein the plurality of structural beams have an axial cross-section in the shape of a triangle, and wherein the plurality of light openings facilitate passage of the UV light emitted from the UV light source.

* * * * *

UNITED STATES PATENT AND TRADEMARK OFFICE
CERTIFICATE OF CORRECTION

PATENT NO. : 12,144,904 B2
APPLICATION NO. : 17/703209
DATED : November 19, 2024
INVENTOR(S) : Jamie J. Childress et al.

Page 1 of 1

It is certified that error appears in the above-identified patent and that said Letters Patent is hereby corrected as shown below:

In the Claims

In Claim 1 at Column 14, Line 60, delete "the plurality of.".

Signed and Sealed this
Seventeenth Day of December, 2024

Derrick Brent
*Acting Director of the United States Patent and Trademark Office*